United States Patent [19]

Schrimm et al.

[11] Patent Number: 4,770,762

[45] Date of Patent: Sep. 13, 1988

[54] ELECTRODE WITH SEALING ASSEMBLY AND FILL HOLE COVER

[75] Inventors: Kenneth J. Schrimm, Bethel Park; Dennis G. Falconer, Gibsonia; Kenneth J. Kato, Export, all of Pa.

[73] Assignee: Fisher Scientific Company, Pittsburgh, Pa.

[21] Appl. No.: 15,442

[22] Filed: Feb. 17, 1987

[51] Int. Cl.$^4$ .................. G01N 27/28; G01N 27/30
[52] U.S. Cl. ..................... 204/435; 204/279
[58] Field of Search ................. 204/435, 279

[56] References Cited

U.S. PATENT DOCUMENTS

| | | | |
|---|---|---|---|
| 3,070,539 | 12/1962 | Arthur et al. | 204/415 |
| 3,088,905 | 5/1963 | Glover | 204/415 |
| 3,445,366 | 5/1969 | Vermeer | 204/435 |
| 3,676,319 | 7/1972 | Kirsten | 204/195 |
| 3,756,936 | 9/1973 | Neuwelt | 204/435 |
| 4,157,289 | 6/1979 | Ikenoue et al. | 204/435 |
| 4,390,406 | 6/1983 | Kato et al. | 204/435 |
| 4,477,330 | 10/1984 | Nielsen | 204/435 |

OTHER PUBLICATIONS

Corning, "Plastic Barrel Combination Electrode", (SF-2 478) (two pages and including Catalog Nos. 476115, 476110, 476101, 476176).
Radiometer Catalog, "Our 50th Year", p. 5 (includes product number GK2501).
Extech, "Portable Meters and Monitors", p. 22 (includes product numbers H60161B, H60161S).

Primary Examiner—T. Tung
Attorney, Agent, or Firm—Alan M. Doernberg

[57] ABSTRACT

An assembly is shown over the top portion of the outer body 14 of a reference electrode or combination pH/reference electrode. An element 50 such as a turning ring covers the fill hole 16 through the outer body 14. In one position of the element 50, a sealing element 24 such as an O-ring forms a passage between fill hole 16 and a through hole 52 through element 50. In other positions of element 50, the sealing element 24 seals the fill hole 16. In embodiments shown, a housing 30 is integral with the cap assembly (60, 70) and aligns the sealing element 24 over the fill hole 16.

12 Claims, 3 Drawing Sheets

ELECTRODE WITH SEALING ASSEMBLY AND FILL HOLE COVER

The preent invention relates to electrodes of the open-junction type, and especially to sealing assemblies for the fill hole through the cylindrical outer body of reference and pH combination electrodes.

Liquid-juntion reference electrodes constructed with a cylindrical outer body (glass or polymer) generally have the junction near the bottom end and the reference cell (e.g., calomel or Ag/AgCl) connected at and entering the outer body from the top end. Electrical connection between the open junction and the reference cell is established by an electrolyte in an electrolyte compartment within the outer body, which electrolyte is slowly depleted by flow through the liquid junction. Electrolyte is periodically replenished through a fill hole extending radially through the outer body near its upper end. For various reasons, it is desirable to cover the fill hole except when the unit is in use or the electrolyte is being replenished.

Conventionally, a cylindrical rubber sleeve is provided around the upper body, covering the fill hole in a normal position, but displaced axially below the fill hole when required. Disadvantages of such cylindrical sleeves include difficulties in use, poor seal and appearance and restrictions placed upon insertion of the electrodes into certain electrode holders.

Separate from the fill hole covering, various components are slipped onto the top of the outer body in order to fix the reference cell and the cable lead in the electrode and to seal the top of the electrode around the cable. Such components typically include banding clips, metal shields and connectors. Conventionally, the rubber sleeve is below and separated from this fixing and sealing assembly.

BRIEF DESCRIPTION OF THE INVENTION

The present invention provides an annular element rotatably mounted outside of and substantially concentric with the outer body through which a first through hole extends horizontally. The annular element is axially aligned with the outer body so that the first through hole is axially aligned with the fill hole in all positions of the fully assembled electrode. In the position for replenishing electrolyte, the annular element is positioned with the first through hole also circumferentially aligned with the fill hole. In at least one other position, the first through hole is circumferentially displaced from the fill hole.

A sealing means is provided for sealing the exterior of the outer body around the fill hole against the interior of the annular element. A second through hole is provided extending radially through the sealing means in axial and circumferential alignment with the fill hole so that, in the position for replenishing electrolyte, the first through hole, second through hole and fill hole form a continuous passage into the electrolyte compartment within the outer body of the electrode. When the annular element is displaced circumferentially from that position, the sealing means and interior of the annular element together form a seal for the fill hole.

Accordingly, the invention provides, in a reference electrode having a cylindrical outer body, an open junction adjacent to the base of and through the outer body, a reference cell within the outer body adjacent to its top and a fill hole extending radially through the outer body communicating with an electrolyte compartment within the outer body, the electrolyte compartment also communicating with the reference cell and the open junction, a reversible sealing mechanism which comprises:

(a) an annular element rotatably mounted outside of and substantially concentric with the outer body, with a first through hole extending radially through the annular element, (b) alignment means for axially aligning the annular element on the outer body with the first through hole axially aligned with the fill hole, and (c) sealing means for sealing the exterior of the outer body around the fill hole against the interior of the annular element to close off the fill hole when the first through hole is not circumferentially aligned with the fill hole, a second through hole being formed radially through the sealing means to connect the first through hole with the fill hole when the first through hole is circumferentially aligned with the fill hole.

DETAILED DESCRIPTION OF THE INVENTION

The present invention will be described, first, in terms of the reference electrode embodiment shown in FIGS. 1-4, then in terms of embodiments where a similar assembly is provided in a combination pH/reference electrode and finally in terms of various contemplated modifications in the assembly. Remarks about both making (assembling) and using the electrode are interspersed throughout the description.

Figure 1:
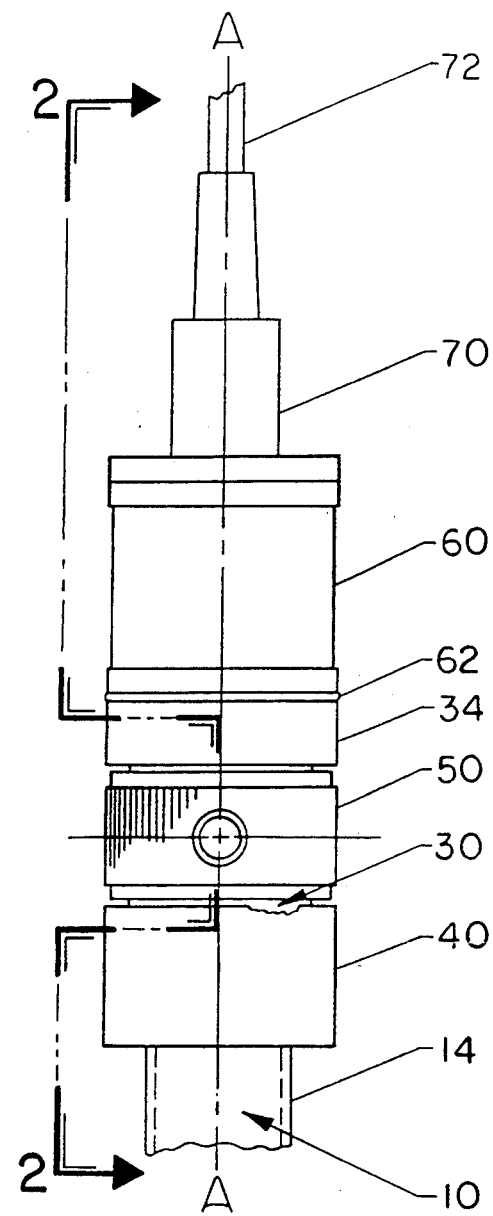
FIG. 1 is a front elevational view of the upper portion of a reference electrode provided with the sealing assembly and fill hole cover of the present invention.
Figure 2:
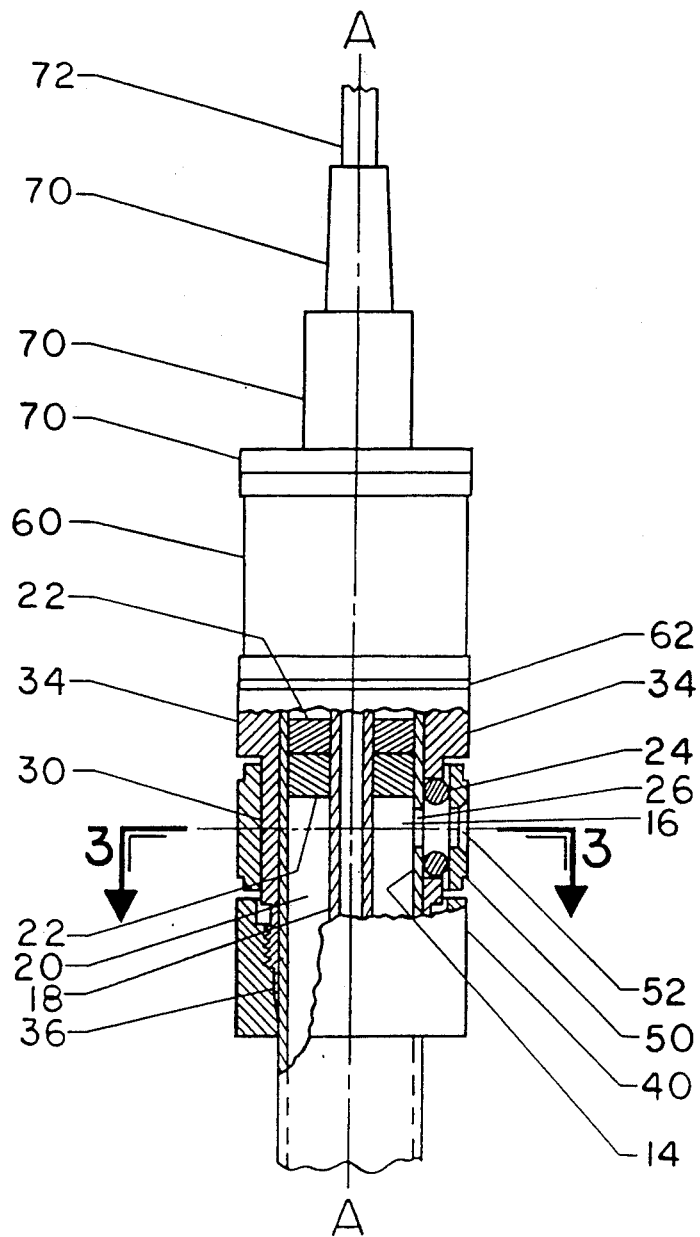
FIG. 2 is a side elevational view, partly in section, along line 2—2 in FIG. 1.
Figure 3:
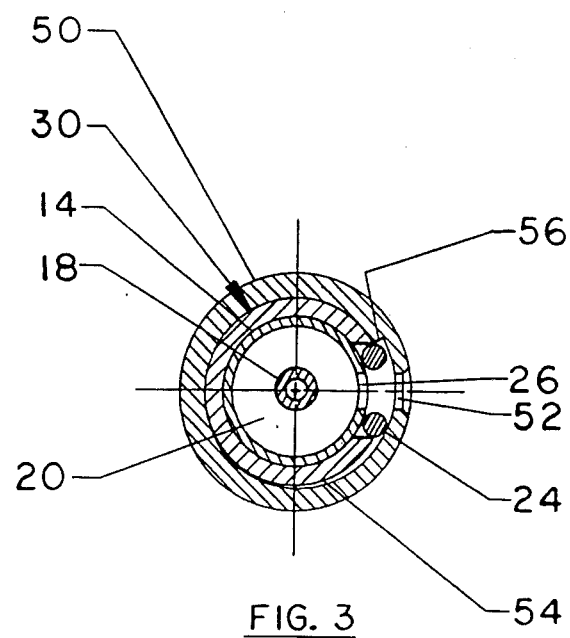
FIG. 3 is a top plan view, in section, along line 3—3 in FIG. 2.

The top portion of a reference electrode 10 is shown in FIG. 1, with a glass or polymer outer body 14 of cylindrical shape around axis A. As best seen in FIGS. 2 and 3, a fill hole 16 extends radially through the outer body 14 with a circular profile when viewed from the front. An inner body 18, shown in FIGS. 2 and 3, is within the upper portion of the outer body 14 and is cylindrical in shape around axis A. The annular space between outer body 14 and inner body 18 is the electrolyte compartment 20. As is conventional when electrode 10 is a single-junction reference electrode, inner body 18 contains the electrochemical reference cell and extends only partially downward from fill hole 16. The electrolyte compartment 20 then occupies the entire interior of the outer body 14 below the lower end of inner body 18 and communicates through an open junction (not shown) with the exterior of the outer body 14 near the base of the electrode 10. Such open junction is sufficiently small for electrolyte to flow out only gradually. So long as electrolyte remains in contact with the cell within inner body 18 to establish electrical connection, replenishment is not required. As shown in FIG. 2, a conventional two part seal 22 around the inner body 18 seals the top of electrolyte compartment 20.

A sealing O-ring is provided around fill hole 16 radially outward of outer body 14. The through hole 26 within O-ring 24 extends radially in alignment with the fill hole 16. The functions of the sealing O-ring 24 are described further below.

A main housing 30 of the sealing assembly is provided around outer body 14 and extends both above and below the fill hole 16. As best seen in FIG. 2, main housing 30 is thickest at an upper collar portion 34 above the axial position of the fill hole 16. Above upper collar portion 34, the main housing 30 has a cylindrical portion with external screw threads (not shown). In certain embodiments, this cylindrical portion is metal or other electrical shielding material joined to or inside of the thermoplastic material (e.g., nylon) of upper collar portion 34. Below upper collar portion 34 is a thin tapered portion 36 of main housing 30, provided with external screw threads. In the preferred embodiment shown, the taper on the exterior of thin tapered portion 36 facilitates compression of thin tapered portion 36 against the outer body 14, as described below, to fix the main housing 30 and other portions of the assembly relative to the outer body 14 in both an axial and circumferential direction. Circumferential alignment can also be established by forming an axially-extending notch on the exterior of the outer body 14 and providing a protuberance on some portion of the main housing 30 that fits in the axially extending notch if and only if proper circumferential alignment exists. A through hole extends radially through the main housing 30 large enough to snugly enclose the O-ring 24, as can be seen in FIGS. 2 and 3. Both the taper and external threads of tapered portion 36 terminate below this through hole in most embodiments.

A lower collar 40 is fitted around the outer body 14 below the fill hole 16 as shown in FIG. 2. The interior of the lower collar 40 is tapered at the same angle as the exterior of tapered portion 36 of main housing 30 and has internal screw threads. Screwing lower collar 40 upward onto tapered portion 36 has the effect, once close contact between the corresponding tapers are made, of compressing the tapered portion 36 against the exterior of outer body 14. Such a means for fixing the assembly relative to the outer body 14 has the advantage of permitting small variances in the external diameter of the outer body 14 to be accommodated: for slightly larger than normal samples of outer body 14, the lower collar 40 is rotated upwardly in a spiral direction a fraction of a turn less than normal. Similarly, for slightly smaller than normal samples of outer body 14, the lower collar 40 is rotated upwardly in a spiral direction a fraction of a turn more than normal.

An annular element or turning ring 50 is provided around outer body 14, concentric with outer body 14 at the height (axial level) of the fill hole 16. In the embodiment shown, it can be seen, especially in FIGS. 2 and 3, that the annular element 50 also surrounds both part of the main housing 30 and the O-ring 24, each of which is sandwiched inwardly of the interior of the annular element 50 and outwardly of the outer body 14. The exterior of annular element 50 is knurled for manual rotation.

The annular element 50 is rotatable around the outer body 14 and main housing 30 but is aligned axially in the fully assembled electrode 10 by the top of the lower collar 40 which engages the bottom of the annular element 50. While the top of the annular element 50 can sometimes engage the bottom of the upper collar portion 34 of main housing 30, it is preferred to leave a small gap therebetween (that is, small relative to the size of the fill hole 16). This enables the annular element 50 to fit on the main housing 30 even if the lower collar 40 is screwed on slightly higher than normal because the diameter of the outer body 14 is slightly smaller than normal. Even then, however, upper collar portion 34 provides a stop that prevents annular element 50 from moving far axially even when the electrode 10 is inverted, as may occur during shipping or use. A through hole 52 is provided radially through annular element 50 in axial alignment with fill hole 16. Even with the small axial movement of annular element 50 permitted by the gap below upper annular portion 34, through hole 52 remains sufficiently aligned with fill hole 16 to form a continuous passage, as shown in FIG. 2, when the circumferential alignment exists.

Referring now to FIG. 3, the annular element 50 is in a circumferential position in which through holes 52 and 26 are aligned with fill hole 16. In this position, electrolyte can be introduced through this passage into the electrolyte compartment 20 within outer body 14. A small inward taper can be formed on the outside of through hole 52 through annular element 50 to help position a tapered dispensing tip of an electrolyte filling vessel and seal around it.

Any rotation of the annular element 50 counterclockwise from the position shown in FIG. 3 will tend to cover or close the passage and thus protect the fill hole 16 from evaporation. The preferred arrangement shown in FIG. 3, however, will also provide a complete seal around fill hole 16 once the annular element is turned counterclockwise at least 40 degrees so that the rate of electrolyte loss through the junction when the electrode 10 is not in use is minimized.

A step 56 is formed on the interior wall of annular element 50. The minimum inner radius of annular element 50 is present counterclockwise from step 56 for at least 185 degrees, and typically for about 190 degrees counterclockwise from step 56 as in the embodiment shown in FIG. 3. Clockwise from step 56, the inner radius of the annular element 50 is at a maximum value for at least the number of degrees of arc corresponding to the width of the O-ring 24. This results in the inner wall of annular element 50 engaging the outer wall of main housing 30 along the major portion where the inner radius is minimal, but being spaced from such outer wall along the minor portion where the inner radius is maximal by a distance sufficient to accommodate the O-ring 24 snugly, but with little or no compression of the O-ring in a direction radial relative to axis A. The inner radius of annular element 50 tapers gradually from the minimal to the maximal inner radius along a tapered section 54 which extends counterclockwise from the major portion to the minor portion, i.e., from the seven o'clock position to the four o'clock position in the position and view shown in FIG. 3.

Figure 4:
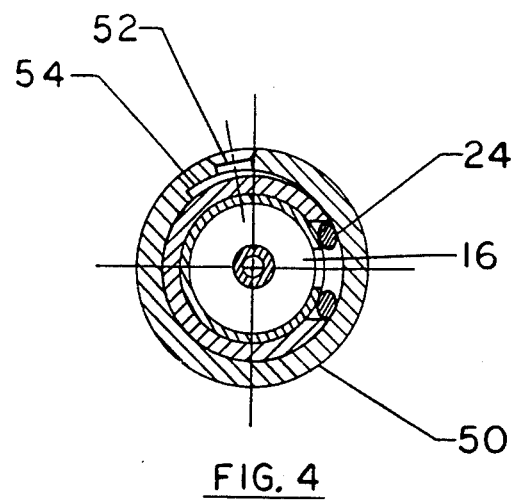
FIG. 4 is a view similar to FIG. 3, in which the annular element has been rotated to seal the fill hole.

Rotation of the annular element 50 in a counterclockwise direction from the position shown in FIG. 3 tends to cover the fill hole 16 by the tapered section 54 of the interior of annular element 50 such as to the position shown in FIG. 4. Since the tapered section 54 then contacts the O-ring 24 by a surface of decreasing radius, relative to axis A, as counterclockwise rotation of annular element 50 proceeds, a tighter seal is established around fill hole 16. FIG. 4 illustrates a typical closed position in which the annular element 50 has been rotated 100 degrees counterclockwise from the position shown in FIG. 3. Various indicia can be provided on the exterior of annular element 50 and upper collar portion 32 or lower collar 40 to indicate the position wherein fill hole 16 is exposed for filling or use and one or more recommended positions in which fill hole 16 is sealed for storage. Furthermore, any change in the size, resiliency or encrusting of O-ring 24 can be compensated for by twisting annular element 50 somewhat less or somewhat more than normal. FIG. 4 shows the full compression achieved by an rotation of annular element 50 over about 90 degrees. Because step 56 engages O-ring 16 in the open position shown in FIG. 3, rotation of the annular element 50 in a clockwise direction is inhibited by the resistance of O-ring 16 to rapid compression from the maximum to the minimum radius at that point of contact. Even, however, if the electrode 10 is misused by rotating the annular element 50 clockwise, subsequent rotation counterclockwise back to the position shown in FIG. 3, or beyond, should enable the O-ring 16 to expand back to a level of compression in the normal range. Alternatively, a stop protuberance in upper collar portion 34 extending into a slot in the top of annular element 50 can prevent rotation of annular element 50 in a clockwise direction from the position shown in FIG. 3.

Referring again to FIG. 2, an upper collar 60 is provided around the upper cylindrical portion of main housing 30, with interior screw threads to engage the exterior screw threads on such upper portion. An optical O-ring 62 can be provided, as shown in FIGS. 1 and 2, between the lower end of upper collar 60 and the upper end of upper collar portion 34 of main housing 30 to establish a moisture-proof seal therebetween as the upper collar 60 is screwed downwardly. A cable relief sealing boot 70, preferably of an elastomeric material, is fitted into the top of upper collar 60 and has stepped sections of reduced radius going upwardly which surround the cable 72. As is conventional, the cable 72 connects the electrochemical half-cell in inner body 18 with external circuitry.

The various components 30, 40, 50 and 60 can be produced in various ways from various materials such as molded . If, for example, molded polyamides (nylon) are used, components 30, 40 and 60 can be rigidified by using filled (e.g., glass-filled) nylon, while element 50 can be made more flexible by using polyamide copolymers with some elastomeric character. Metal shielding can be provided on the top of component 30 by attaching (e.g., by sonic welding) a metal piece, inserting a metal piece or applying conductive paint to a plastic piece. Various elastomers can be used for rings 16 and 62, although it is preferred to use a high quality rubber for O-ring 16 because of its repeated compression and release.

In assembling the electrode 10, normally all of the components shown, except for O-ring 24, are strung onto cable 72 in the order shown, with elements 40 and 50 below the main housing 30, and elements 60 and 70 above the main housing 30. If the upper portion of main housing 30 is a different material (e.g., metal) than the remainder of the main housing 30, then it may be affixed before stringing onto the cable 72 or may be affixed later in the process. Similarly, boot 70 can be fitted into upper collar 60 before or after stringing onto cable 72.

Then the electrical connection between cable 72 and inner body 18 is made. The inner body 18 has previously been positioned within outer body 14 at the desired position and the two-part seal 22 has been formed, typically by first inserting a porous lower section for support and then adding and curing the upper section. Usually this seal is formed before attaching the cable 72.

Once the seal 22 is formed and the cable 72 attached, components 40, 50 and 30 are slid down around the outer body 14 at or below their final positions. The top of the interior of outer body 14 is then filled with a potting material and elements 60 and 70 are slid down on top of the outer body 14 to complete the upper seal. At this point, upper collar 60 and the upper section of main housing 30 are screwed together, so as to position the metal shielding at the desired height (axial position) and establish the lower end of portion 34 of main housing 30 at the desired height (axial position), with the through hole through the main housing 30 surrounding fill hole 16. The O-ring 24 can then be positioned within the through hole through main housing 30 so that through hole 26 through O-ring 24 is aligned with fill hole 16.

The annular element 50 is then rotated to the circumferential position shown in FIGS. 2 and 3 and brought axially upward around the main housing 30 and O-ring 24 generally into the axial position shown in FIGS. 1 and 2. The lower collar 40 is then brought upward axially until it engages the external screw threads on tapered lower portion 36 of main housing 30. The lower collar 40 is then screwed upwardly until the tapered lower portion 36 is compressed tightly around and against the exterior of outer body 14. The annular element 50 can then be checked for alignment with fill hole 16 and rotatability.

While the above description has applied to electrode 10 as a single-junction reference electrode, the application of the invention both to double-junction reference electrodes and to combination electrodes should be apparent. The primary changes for a double-junction reference electrode would involve a tube containing the half-cell, electrolyte (liquid or gelled) and an open junction replacing the inner body 18 and leading into electrolyte compartment 20 and modifying the two-part seal 22 accordingly. In the case of a combination pH/reference electrode, the inner body inserted would be a tube sealed to the interior of the outer body. The interior of the tube would form a central chamber and terminate in a pH sensing membrane which contacts the sample being measured. This central chamber would receive an element forming a half-cell. Electrolyte chamber 20 would also receive a half-cell element and form the reference side of the combination electrode. Similarly, the electrode could be modified for use as a reference electrode for an ion-selective electrode.

In each case, an appropriate cable 72 (e.g., co-axial cable when electrode 10 is a combination electrode) would be used and connected where appropriate at the appropriate time. Some modification in boot 70 can be used to accommodate different cable sizes, while using a standard size of upper collar 60 and various other components. Thus, the present invention enables a varied line of electrodes to be manufactured with many common components so long as a standard outside diameter of outer body 14 is maintained. The interior of the upper section of the main housing 30 and the upper collar 60 can also be designed to receive a detachable cable system connector instead of upper boot 70 provided that electrical connection has been provided between the half-cell within body 18 and a termintion on the upper end of main housing 30.

The particular combination and design of upper collar 60, main housing 30 and lower collar 40 shown in the preferred embodiment depicted in the Figures is one of many that can be used to position and align annular element 50 for free rotation, but a relatively fixed axial position, relative to fill hole 16 through outer body 14. For example, upper collar 60 could extend downwardly over the top of the main housing 30 and directly form the alignment flange that restricts upward movement of the annular element 50.

The O-ring 24 is a preferred geometry of sealing means, especially when a fill hole 16 of circular profile is used and especially in combination with the offset and tapered inner wall of annular element 50 shown in FIG. 3. Even, however, in this environment, the O-ring 24 could be modified by, e.g., flattening its exterior so as to have a backwards "D" shape in the view shown in FIG. 3. Other shapes of sealing means (e.g., square) could be provided and accommodated by a different shape of hole through main housing 50. Even a different shape of through hole 26 (e.g., oval) could be used, whether or not the circular shape of the fill hole 16 is maintained.

A modified use of the present invention would be to redesign the cap assembly so that, instead of annular element 50, which is axially aligned, but rotatable, an element would be provided that is circumferentially aligned, but movable vertically (axially). In such case, the O-ring 24 would form a passage between the fill hole 16 and a through hole in the element in one vertical position of the element but would seal the fill hole against the interior of the element in other vertical positions of the element. The interior of the element could be tapered to compress the O-ring as the element is moved away from the open position.

We claim:

1. In a reference electrode having a cylindrical outer body, a reference cell within the outer body adjacent to its top and a fill hole extending radially through the outer body communicating with an electrolyte compartment within the outer body, the electrolyte compartment also communicating with the reference cell and the open junction, a reversible sealing mechanism which comprises:
   (a) an annular element rotatably mounted outside of and substantially concentric with the outer body, with a first through hole extending radially through the annular element,
   (b) alignment means for axially aligning the annular element on the outer body with the first through hole axialy aligned with the fill hole, and
   (c) sealing means for sealing the exterior of the outer body around the fill hole against the interior of the annular element when the first through hole is and is not circumferentially aligned with the fill hole, to close off the fill hole when the first through hole is not circumferentially aligned with the fill hole, a second through hole being formed radially through the sealing means to connect the first through hole with the fill hole when the first through hole is circumferentally aligned with the fill hole.

2. The reference electrode of claim 1 wherein the sealing means is an elastomeric O-ring.

3. The reference electrode of claim 1 where the alignment means comprises a lower collar around the outer body, an upper edge of the lower collar engaging a lower edge of the annular element.

4. The reference electrode of claim 3 wherein the alignment means further comprises an upper collar whose lower edge is in close proximity to an upper edge of the annular element.

5. The reference electrode of claim 4 wherein a housing is provided around the upper portion of the outer body, an enlarged through hole being formed and extending radially through the housing aligned with the fill hole, and the sealing means being contained within the enlarged through hole.

6. The reference electrode of claim 5 wherein the upper collar is integral with the housing.

7. The reference electrode of claim 3 wherein the interior of the lower collar is tapered and threaded, the lower end of the exterior of a housing around the sealing means is threaded and tapered such that the mating of the exterior and interior threads compresses the lower end of the housing against the outer body and aligns the housing relative to the outer body.

8. The reference electrode of claim 7 wherein the housing is integral with a cap assembly on the top of the outer body.

9. The reference electrode of claim 1 wherein an interior recessed portion is formed in part of the circumference of the annular element and the sealing means is received within the interior recessed portion.

10. The reference electrode of claim 9 wherein the sealing means abuts a first end of the inner recessed portion when the first through hole is in circumferential alignment with the fill hole.

11. The reference electrode of claim 10 wherein the sealing means is elastomeric and the recessed portion is tapered to have a greatest radius at the first end and a progressively smaller radius away from the first end whereby the elastomeric sealing means is compressed as the annular means is rotated away from a circumferential position in which the first through hole is aligned with the fill hole.

12. The reference electrode of claim 11 wherein the sealing means is an elastomeric O-ring.

* * * * *